United States Patent
Miethke

(10) Patent No.: US 7,422,566 B2
(45) Date of Patent: Sep. 9, 2008

(54) METHOD OF TREATING A PATIENT WITH HYDROCEPHALUS AND APPARATUS THEREFOR

(75) Inventor: Christoph Miethke, Kleinmachow (DE)

(73) Assignee: Christoph Miethke GmbH & Co. KG, Potsdam (DE)

( * ) Notice: Subject to any disclaimer, the term of this patent is extended or adjusted under 35 U.S.C. 154(b) by 100 days.

(21) Appl. No.: 11/149,928

(22) Filed: Jun. 10, 2005

(65) Prior Publication Data

US 2007/0004999 A1    Jan. 4, 2007

Related U.S. Application Data

(63) Continuation-in-part of application No. PCT/EP03/13999, filed on Dec. 10, 2003.

(51) Int. Cl.
*A61M 5/00* (2006.01)
(52) U.S. Cl. ................. 604/9; 604/264; 604/8
(58) Field of Classification Search ........ 604/8, 604/9, 264, 247, 248; 251/89
See application file for complete search history.

(56) References Cited

U.S. PATENT DOCUMENTS

| | | | |
|---|---|---|---|
| 3,985,140 A * | 10/1976 | Harris | 604/9 |
| 4,540,400 A * | 9/1985 | Hooven | 604/9 |
| 4,676,772 A | 6/1987 | Hooven | |
| 4,772,257 A * | 9/1988 | Hakim et al. | 604/9 |
| 4,781,673 A * | 11/1988 | Watanabe | 604/9 |
| 4,867,740 A * | 9/1989 | East | 604/9 |
| 5,637,083 A * | 6/1997 | Bertrand et al. | 604/9 |
| 5,643,194 A | 7/1997 | Negre | |
| 5,928,182 A * | 7/1999 | Kraus et al. | 604/9 |
| 6,840,917 B2 * | 1/2005 | Marion | 604/9 |
| 2004/0010219 A1 | 1/2004 | McCusker et al. | |

FOREIGN PATENT DOCUMENTS

EP    0 421 557 A2    4/1991

* cited by examiner

*Primary Examiner*—Leslie R Deak
(74) *Attorney, Agent, or Firm*—Nils H. Ljungman & Associates

(57) ABSTRACT

An adjustable hydrocephalus valve comprising a mechanical brake. The brake can be decoupled by pressing the valve housing percutaneously and allows in this state to adjust the opening characteristics of the valve by rotating externally disposed magnets. In order to detect the adjusted pressure or in order to adjust the pressure, specific adjustment or measuring pin principles are presented which simplify and at the same time improve the respective functions of measuring and adjusting.

20 Claims, 8 Drawing Sheets

METHOD OF TREATING A PATIENT WITH HYDROCEPHALUS AND APPARATUS THEREFOR

CONTINUING APPLICATION DATA

This application is a Continuation-in-Part application of International Patent Application No. PCT/EP2003/013999, filed on Dec. 10, 2003, which clams priority from Federal Republic of Germany Patent Applications No. 102 58 070.7, filed on Dec. 11, 2002, and No. 103 47 278.9, filed on Oct. 8, 2003. International Patent Application No. PCT/EP2003/013999 was pending as of the filing date of this application. The United States was an elected state in International Patent Application No. PCT/EP2003/013999.

This invention relates to a percutaneous adjustable hydrocephalus valve to equalize the pressure in the cranium of a hydrocephalus patient by the drainage of excess liquor into the patient's peritoneum (abdominal cavity) or heart.

Hydrocephalus patients have the following medical problem: The brain is surrounded by a special liquid called liquor. This liquor is formed in symmetrically located chambers of the brain, flows through ventricles into the outer subarachnoid space, where it is resorbed. Normally there exists equilibrium between the amount of fluid that is produced and the amount that is resorbed. In the illness hydrocephalus (also called water on the brain), this equilibrium is disrupted and a sufficient amount of fluid is no longer resorbed. This condition results in an increase in pressure inside the patient's head. In infants, this condition results in abnormal growth of the head; the brain decreases in size and the interior of the patient's skull is increasingly filled only with liquor. In adults, no further growth of the head is possible and critical pressure levels are reached quickly. The brain is weakened by the presence of the excess fluid. In adults, this condition can cause problems in the patient's gait, urinary incontinence and dementia.

Since the 1950s, hydrocephalus has been treated successfully by the implantation of an artificial drainage system. In this case, an artificial connection is created between the chambers in the brain and a drainage medium. As a rule, the peritoneum (the abdominal cavity) is currently most often used. Alternatively, drainage into the right atrium of the heart is also conventional. Special valves are integrated into these systems, the purpose of which is to control the drainage of fluid. Since the introduction of artificial drainage in hydrocephalus therapy in the early 1950s, numerous different valve systems have been proposed to optimize the result of the treatment.

In recent years, the attention of specialists in the field has been increasingly focused on two competing valve designs: on one hand, percutaneous adjustable valves in which the opening characteristic can be adjusted to individual patient requirements, and on the other hand valves that guarantee an opening characteristic that varies as a function of the position of the valve.

Valve systems of the latter type have a significantly higher opening pressure when the patient is in the standing position than in the reclining position. Both valve systems are currently used with great success for the treatment of hydrocephalus.

A combination of the two types of valves is desirable. In the context of the invention, a combination of this type is now specifically proposed, whereby the known problems are solved by means of available adjustable valve systems.

The essential problems of the adjustable valves of the prior art lie in the accuracy and precision of the adjustment and in protection against unintended adjustments of the valve system caused by external magnetic fields. All the adjustable valves of the prior art are based on a magnetic principle. On the valve side, magnets of different sizes are attached to a rotationally mounted rotor. The position of these rotors can be influenced by externally generated magnetic fields, which results in an adjustment of the bias of a spring.

The best-known valves include the Medos-Codman valve. This valve contains a leaf spring which is in contact on one side with a ruby ball which is pressed by the leaf spring into the valve seat and on the other side is in contact with a stepped rotating rotor. The fastening of the leaf spring is located between these two points—approximately in the middle. If the rotor is then rotated by magnetic fields from outside, the contact point and the opening characteristic changes and the opening characteristic of the valve is therefore adjusted. The adjustment range lies between the pressure of a column of water 3 and approximately 20 cm high. The outside diameter of the rotor is approximately 3 mm. The range of rotation of this valve is 360 degrees. This valve exhibits the following systematic problems:

The setting can be unintentionally changed by externally applied magnetic fields.

This change can only be verified by means of X-rays.

Precisely for the patients effected, the necessary MRT examinations, especially for infants, therefore entail the X-ray verification of the pressure level to which the valve is set. This procedure represents undesirable stress on these patients and therefore limits the use of this type of valve.

The adjustable SU8 manufactured by the French company Sophysa is another of the best known adjustable valves. Here, too, valve-side magnets are located on a rotating rotor. The position of the rotor can be modified by external magnetic fields.

The pressing of the sapphire ball thereby defines the valve characteristic. If the rotor is rotated, the resulting free clamped length of the leaf spring changes, and along with it the opening pressure.

A short free clamped length results in a high opening pressure, and a long free clamped length in a low opening pressure. Here, too, the adjustment range is between the pressure represented by a column of water between 3 and 20 cm high. The adjustable range of rotation is approximately 90 degrees, i.e. the setting of 0 degrees guarantees the minimum pressure, for example, while the setting of 90 degrees guarantees the maximum pressure. The essential weak points of this design consist on one hand of precisely this narrow adjustment range, because the accuracy of a system of this type is smaller, the smaller the angle of rotation used. This valve also has the disadvantage that external magnetic fields can cause an unintentional rotation and adjustment of the opening characteristic. With this design, however, an X-ray verification is not necessary. For that purpose, the unintentional adjustment can be caused extremely easily, e.g. by the magnetic fields of headphones or by simple bar magnets.

On account of these known problems, Sophysa recently presented a new development, which it designated the Polaris Valve. This valve is largely similar to the known valve, although it has an additional magnetically activated blocking mechanism, as a result of which only a very specific arrangement of externally attached magnets can cause the rotor to rotate.

A third adjustable valve, the Strata Valve, is sold by Medtronic (PS Medical). Like the models described above, two magnets are attached on the valve side that are integrated into a rotor.

External magnetic fields make it possible to rotate this rotor and to adjust the opening characteristic of the valve. This valve can be adjusted in four stages. The rotor is rotated by the attraction of the rotor to the externally applied magnetic field and subsequent rotation. Only when the rotor is attracted by the magnets can it be rotated. This valve also contains a sort of magnetic locking mechanism. As a result of the rotation of this rotor, the overall height of the rotor is varied. The higher the rotor is mounted on a sort of staircase, the higher the opening pressure. A mechanism of this type may limit the possibility of unintended adjustment, although it can never function 100% safely or reliably.

All the valves described above have one or more of the problems described below:
1. Setting errors
2. Readout errors with regard to the opening pressure that has been set.
3. Unintentional adjustment
4. Functional weaknesses.

The invention is nevertheless based on the constructions of the prior art, and the object of the invention is to create a valve that is easy to operate and safe. This valve is designed, as in the prior art, in the form of an internal, percutaneously activated adjustment device that is moved with an external adjustment device.

Figure 1:
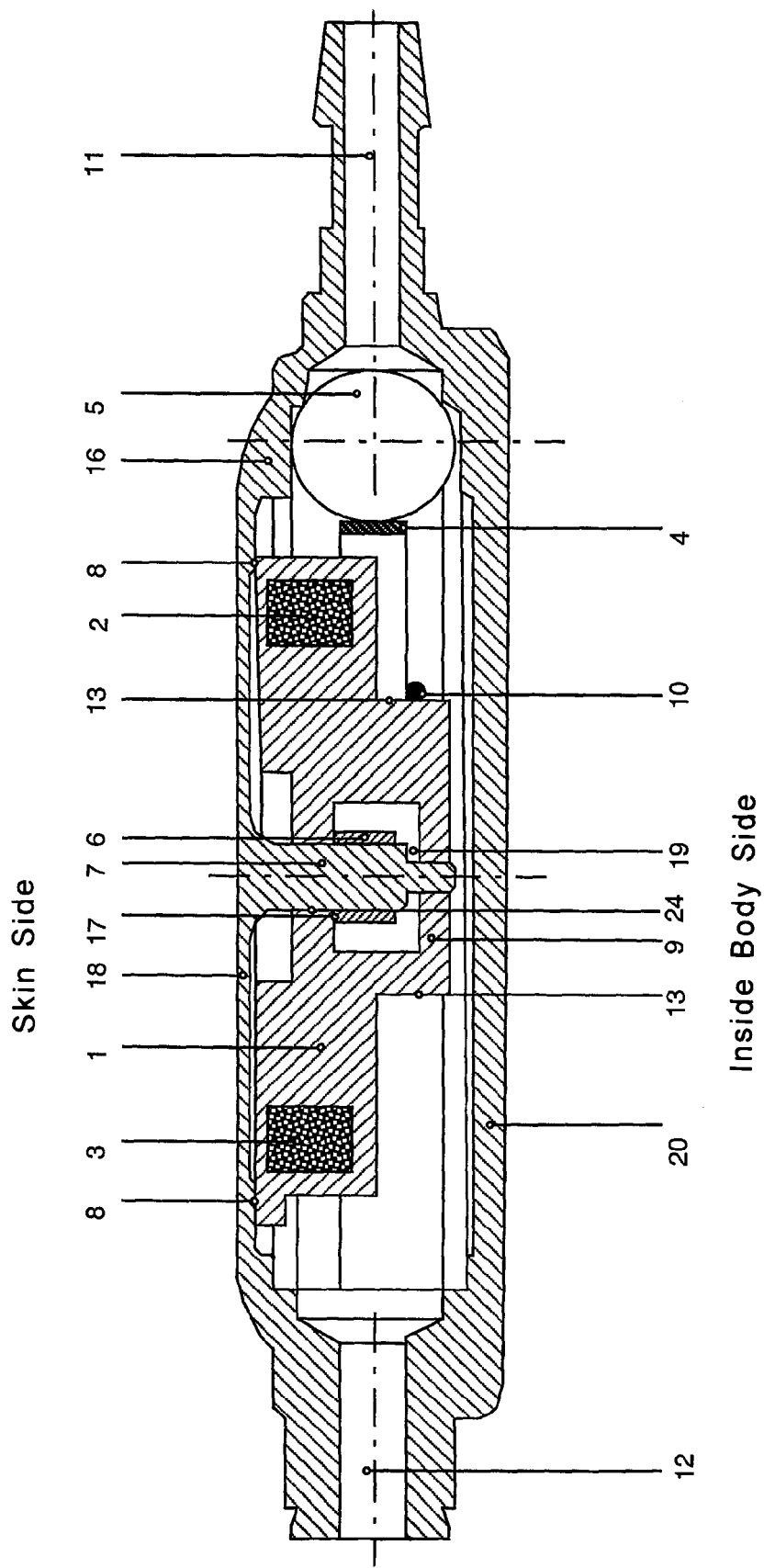
FIG. 1 shows a cross-sectional view of a hydrocephalus valve arrangement according to at least one possible embodiment.

The invention therefore teaches that the internal adjustment device inside the valve is prevented from unintentional adjustment movements by a frictional engagement in the deactivated position. The frictional engagement is created by the corresponding pressure of the friction surfaces, one of which is stationary and is preferably a surface on the valve housing, while the other friction surface corresponds to the adjustment device in the valve.

The pressure that corresponds to the frictional engagement can be created: a) by the load of a spring pressure and/or b) by magnetic force. The spring provided in a) is preferably formed by the valve housing itself.

For this purpose, the valve housing can have a flexible housing wall and a rotationally movable adjustment mechanism that is held centrally at a certain distance from it. The adjustment mechanism can be realized in the form of a adjustment plate or in the form of a one-armed or multi-armed lever, rotor or molding. The remainder of this description uses only the term "adjustment plate", although the term as used is intended to include all other potential realizations.

The distance from the housing wall must then be selected so that the adjustment plate, in the inactivated position, is pulled or pushed by means of its outside edge against the housing wall. The related tension in the housing wall is created when the housing wall is indented during the installation of the adjustment plate. After the installation, the housing wall can return only partly to the original shape on account of the presence of the adjustment plate. On account of the spring material of which the housing wall is made, the housing wall nevertheless attempts to return to its initial shape prior to the assembly or installation. That creates the desired pressure of the adjustment plate against the housing wall.

The housing wall can be straight and can assume a concave shape as a result of the deformation/impression described above. The housing wall can also be originally curved concavely and can experience an additional inward curvature as a result of the deformation/indentation described above.

The housing wall can also originally be convex and as a result of the deformation/indentation can experience a total elimination of the convex curvature. Optionally, an inward curvature can also result from the deformation/inward curvature of an initially convex shape.

The application force can be influenced by the thickness of the housing wall, by the mass of the original configuration, by the material of the housing wall and by the distance of the adjustment plate from the housing wall. The application pressure can be further optimized with a few tests.

As explained under b) above, the application pressure can be created by permanent magnets of the adjustment device in the valve instead of or in addition to the above mentioned springs. When a material that reacts to the magnetic fields of the permanent magnets is used for the housing wall, the resulting application pressure of the adjustment plate is a function of the power of the permanent magnets. Steel is particularly well-suited for use as the material of the housing wall.

The arresting of the valve in the deactivated position is further influenced c) by the selection of the diameter of the adjustment plate and/or d) by the characteristics of the friction surfaces. A higher friction can be achieved by rough friction surfaces. For this purpose, the arresting surfaces can optionally be roughened or coated with a friction-enhancing material.

The greater the diameter over which the friction surfaces are in contact with the housing wall, the greater the arresting effect.

In one advantageous realization, the adjustment plate assumes a more or less pronounced U-shape when viewed in cross section. In that case, the housing wall corresponds with a ring-shaped raised portion that is provided on the outer edge of the adjustment plate.

The frictional engagement claimed by the invention can advantageously be neutralized e) by a counterpressure.

By means of such a counterpressure, sufficient distance can be created between the friction surfaces so that the adjustment device that lies within the valve can move freely.

The counterpressure that is necessary to neutralize the frictional engagement is preferably applied manually and can be created by f) the deformation of the spring that is responsible for the spring force according to a) and/or g) by the neutralization of the magnetic force. When the housing wall forms one of the springs, the counterpressure is generated by external pressure applied against the housing wall. The necessary counterpressure can be determined at the factory and can be checked when the valve is adjusted.

Suitable measurement devices for the measurement include h) mechanical measurement devices and i) electrical measurement devices. A purely mechanical measurement device can be realized in the form of an adjustment pin that has a flexibly mounted tip. The necessary counterpressure can be measured and excessive counterpressure can simultaneously be prevented by controlling the spring travel.

The electrical measurement device can, for example, use a current-carrying strain gauge. The resistance of the strain gauge varies as a function of the load applied to it, as a result of which the current or the voltage varies. The counterpressure is measured by measuring the variation. This capability can also be used to emit an optical and/or acoustic signal when a minimum counterpressure is reached, which signal continues to be emitted as long as the maximum counterpressure is not exceeded, or when the maximum counterpressure is exceeded, is supplemented by an additional optical and/or acoustical signal.

The counterpressure is optionally limited to the allowable magnitude by: j) an interposed spring element. In that case, the spring element is provided in the external adjustment device. The spring element optionally consists of a long-stroke, biased spring. With this adjustment device, when the spring bias is appropriately designed, a resilience of the adjustment device becomes noticeable when the necessary pressure is reached at which the adjustment plate lifts up from its corresponding friction surfaces. The allowable pressure is only exceeded when the resilience of the external adjustment device is no longer measurable. In between there is a significant resilience range in which the treating physician can be confident during the manipulation of the valve that he is in the range of allowable pressure.

The valve adjustment is preferably performed after the adjustment plate has been loosened by: k) rotating the adjustment plate. Even greater preference is given to a greater adjustment travel between the minimum opening position and the maximum opening position of the valve, which increases the safety of the adjustment and the accuracy of the adjustment.

The long adjustment travel is translated into a modification of the spring load. In other words, with a comparable range of variation of the spring load, there is a longer adjustment travel. The risk of unintentional adjustment mentioned above decreases by the extent to which the adjustment travel becomes greater.

The precision of the adjustment preferably increases as the adjustment travel becomes greater.

The ability to make the adjustment travel longer results from a variation of the position of the spring. The invention teaches that the spring is designed so that its plane of movement lies parallel to the plane of rotation of the adjustment plate. The invention also teaches that this parallel condition is also present when the planes coincide.

As a result of the location and orientation of the spring as claimed by the invention, the spring can move in the direction in which the valve housing is at the point of its farthest travel, which in this case is the direction of the flat side.

The spring used is preferably a spring rod that is mounted so that it can pivot.

The spring rod can form a two-armed lever, the one end of which is longer than the other end. It is thereby possible to effect a step-up or step-down transmission of the lever movement or of the lever force. The one end of the lever is effectively connected with a valve ball or a valve shutter of the valve, and the other end interacts with the adjustment mechanism or the adjustment plate described above.

There is preferably a sliding virtual connection, of the type that is itself known from the prior art, between the spring and the corresponding surface on the adjustment plate. In other words, the spring slides on the contact surface of the adjustment plate.

The virtual connection with the valve ball or the valve shutter is created by the short end sliding against the valve ball or pressing against the valve ball.

The virtual connection with the adjustment mechanism is formed by the provision of a sliding surface for the other lever arm on the rotational or pivoting part. This sliding surface is realized in the form of a curved path on which the spring rod is in sliding contact. The curved path makes it possible to give the valve a valve characteristic that can be adjusted within broad limits. The curved path preferably runs at least partly in a spiral shape. The peripheral angle of the curved path on the sliding contact surface of the adjustment plate preferably covers at least 300 degrees, and even more preferably 340 degrees.

Depending on the lever ratios, the movement of the lever arm that is in contact with the curved path of the adjustment plate is stepped up or stepped down to the other lever arm that is in contact with the valve ball or valve shutter.

Depending on the design of the valve ball or of the valve shutter, there is a retraction or adjustment of the corresponding lever arm. Or there is a variation of the application pressure of the lever arm against the valve sphere or valve shutter.

The direction of rotation of the adjustment plate determines the direction in which the lever pivots.

When there is a back-and-forth movement of the adjustment plate, there is also a back-and-forth pivoting movement of the lever in the direction of a minimal opening width or of a minimal closing pressure on the valve or vice-versa in the direction of the maximum opening width or of the maximum closing pressure.

Optionally the adjustment plate can also be moved farther in the same direction of rotation and still return to the beginning of the adjustment movement. This feature results from the fact that a transition or transfer is provided between the beginning of the curved path and the end of the curved path on rotating or pivoting adjustment plate.

From the above description it is apparent that to reach a valve position, the valve taught by the invention can be rotated both over the shortest distance into the new valve position as well as in the opposite direction of rotation to the end of the curved path and beyond into the new valve position. The latter operation can be desirable when every valve setting must be used for the control of the beginning of the adjustment movement or the beginning of the curved path.

The two-armed spring lever taught by the invention preferably has an angled shape. The two lever arms of the two-armed lever arm are at an angle to each other that can be less than 180 degrees and can even be less than 90 degrees.

The cross section of the spring taught by the invention can be anything that is desired. Round and rectangular shapes are advantageous. A spring with a leaf-shaped or wire-shaped cross section is particularly advantageous.

For the pivoting or rotational mounting of the spring, a pin can be used, for example one where the ends of the pin are engaged in corresponding recesses in the valve housing or in the valve cover or valve base. The ends of the pin can also be sharp, so that the pin can rotate on the tips in the recesses. This method is technically and economically advantageous.

To fasten the pin to the spring, a welded or soldered connection can be used, and other types of connections are also suitable.

The spring taught by the invention can also be in direct contact with the curved path or the adjustment plate, even when a spring wire is used.

On the valve-ball side it is favorable to have contact take place between the spring and valve ball over a large-area surface. If and to the extent that the spring does not permit contact over the desired large area, a plate can be fastened to the end of the spring in question. The plate can be optionally welded or soldered on, or can also be fastened in any other suitable manner.

The rotation of the adjustment plate that is necessary for the adjustment of the valve preferably takes place by means of additional externally located magnets and an external rotation device. The magnets are preferably permanent magnets. Even greater preference is given to the use of two magnets that are diametrically opposite each other in the adjustment plate and at least as many magnets in the rotation device, likewise arranged opposite each other, whereby the magnets of the adjustment plate lie on an orbit, the diameter of which is equal to the diameter of the orbit on which the magnets of the rotation device lie. The various magnets can thereby be brought as close as possible to each other. As a result of their geographic proximity, the magnets can exert optimal forces. The torques that are necessary for the creation of a torque are produced when the markets face one another with opposite poles, e.g. with a south pole in the rotation device and a north pole in the adjustment plate.

In the device claimed by the invention, even relatively small magnets can exert sufficient force for the valve adjustment.

The rotational device is advantageously also used as an adjustment device, for this purpose, the device described below is used, with which not only can the rotation described above be achieved, but the pressure described above can also be exerted.

After an adjustment of the valve by rotating the adjustment plate, the adjustment plate is arrested in the respective rotational position. The arresting occurs when the load is once more removed from the previously indented housing wall. Then the application of pressure described above and the related friction occur again.

In the arrested position of the adjustment plate, the magnets reinforce the arresting by increasing the application pressure and the friction between the adjustment plate and the valve housing. For this purpose, the surface nearest to the magnets is preferably realized in the form of a reactive metal surface. Steel surfaces are especially reactive.

The additional arresting forces effected with the magnets enclosed in the valve as taught by the invention advantageously do not interfere with the valve adjustment with external magnets, because as a result of the counterpressure described above, the magnetic force is easily overcome and the necessary distance of the adjustment plate from the corresponding housing wall can be established.

The magnets used are preferably small models such as pin magnets of the type disclosed in claims. The small magnets also contribute to the achievement of small valve dimensions, as disclosed in the claims.

The adjustment device for the valve taught by the invention can also be realized with extremely small dimensions. The invention teaches that this feature is used to reduce the diameter of the adjustment device and for a special shaping of the valve device, namely for the configuration of the adjustment device in the shape of a pin, similar to a ball-point pen. The realization of the adjustment device similar to a ball-point pen makes it possible to operate the adjustment device in the same manner as a pin or a ball-point pen, e.g. by carrying it in a breast pocket. Likewise, a mechanism like that in a ball-point pen can be used to move the magnets that are provided on the head of the adjustment device in the longitudinal direction of the pen forward (when the pin is placed against the patient's head or against the valve) or back. In the vertical position of the pin, that means raising and lowering.

The pin-shaped external adjustment device claimed by the invention has, on the front end, a cap with which the adjustment device is applied. When the adjustment device is applied loosely, the magnets automatically center the adjustment device so that it is easy to actuate the adjustment device by rotating it.

The advantages of the valve and its adjustment device as taught by the invention are:
1. Precise adjustment of the pressure characteristic by use of the largest possible adjustment angle,
2. Readout of the opening pressure set without X-ray detection,
3. Prevention of an unintentional adjustment of the valve,
4. Increase of the general safety and reliability of operation.

FIG. 1 shows a schematic cross section drawing of the invention enlarged several times. The valve consists of a sturdy titanium housing 16 into which a valve 11 has been introduced. The sapphire ball 5 is pressed into the valve seat by the leaf spring 4. The leaf spring 4 forms a functional unit with the spring wire 3 and a shaft 15 that is visible in FIG. 2. In the adjustment plate that is designated the rotor 1, two magnets 2 and 3 are introduced with opposite polarity. The rotor 1 is held on a shaft 7. The shaft 7 is located on a base 18 of the titanium housing 16. The base 18 is curved.

The rotor 1 is clamped by a screw 6 on the shaft 7 against the cover so that the rotor 1 is pressed against the base 18 and is bent elastically. The pressure is applied so that the friction force suffices to prevent a rotation of the rotor 1 caused by external magnetic fields. The base 18 preferably has a thickness of 0.1 to 0.2 mm, and in other exemplary embodiments a thickness of up to 0.5 mm. The elastic deformation connected with the bending preferably amounts to from 0.01 mm to approximately 0.1 mm, and in other exemplary embodiments up to twice the thickness of the base. The more bias is applied to the base, the more force must later be applied from outside to effect a lifting of the rotor 1 at 6 from the base 18 and to neutralize the arresting of the rotor 1 on the base 18.

The position of the rotor 1 defines the force that the leaf spring 4 exerts on the sapphire ball 5.

Figure 2:
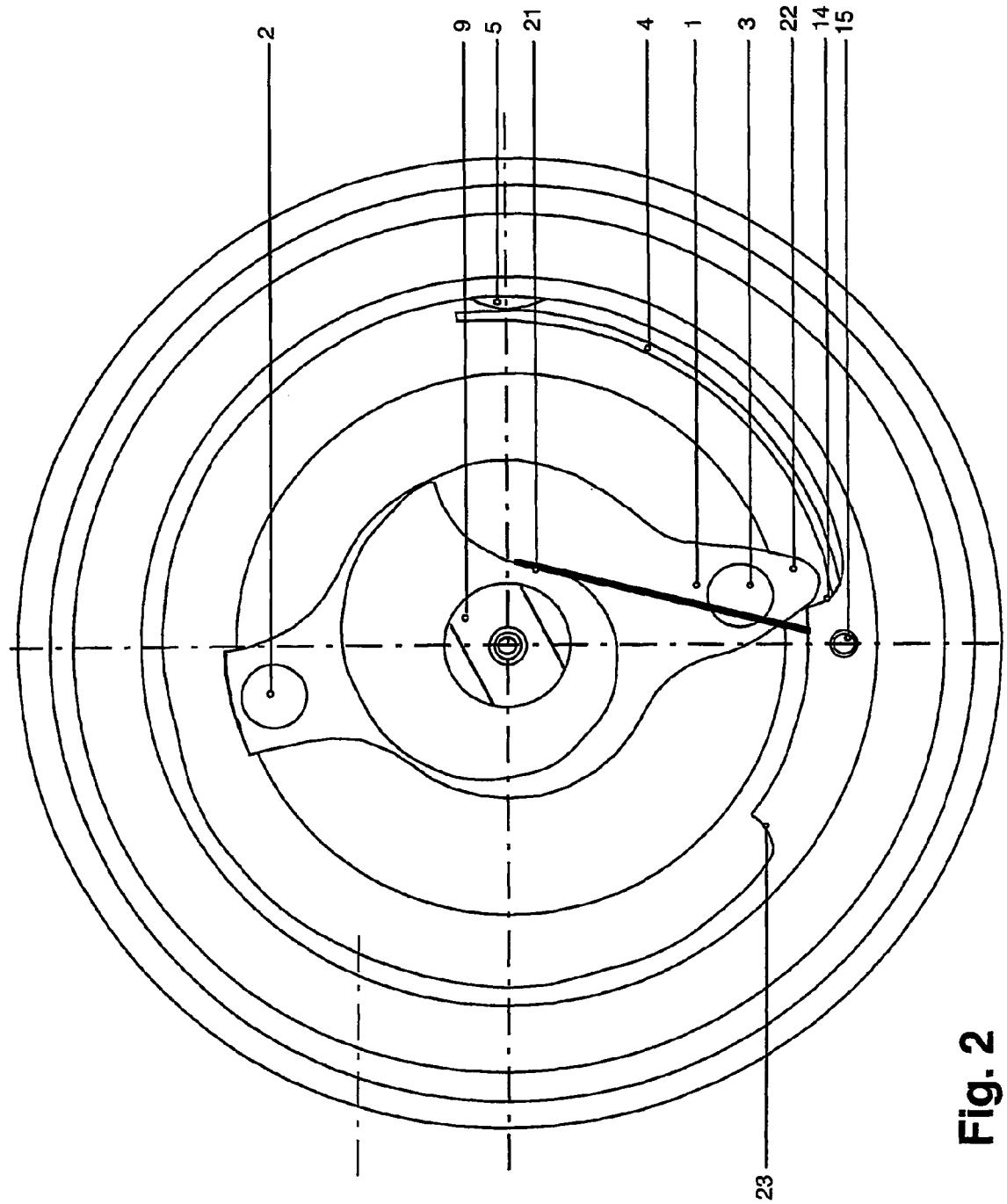
FIG. 2 shows a view of a rotor device of a hydrocephalus valve arrangement according to at least one possible embodiment.

FIG. 2 is a view of a valve that is open on the bottom. The figure shows the spring 10 which is welded to the shaft 15 and the leaf spring 4. These components are preferably made of a metal material, in particular of titanium or a titanium alloy.

The spring wire of the spring 10 preferably has a diameter of 0.1 mm, and in other exemplary embodiments the spring wire can have a smaller cross section for shorter lengths and a larger cross section for longer lengths. The cross section of the spring wire in the exemplary embodiment is circular. The leaf spring also preferably has a thickness of 0.1 mm and a height of approximately 1 mm. For other exemplary embodiments with smaller lengths and longer lengths, the information regarding the wire of spring 10 applies as appropriate.

The leaf spring is very stiff.

The shaft 7 has, on the left in the drawing, a shoulder and lugs with which it projects into a smaller hole of the part 9 on the rotor 1. When the device is assembled, there is a gap in position 19 between the shaft 7 and the part 9.

In FIG. 1, the skin side is to the right in the drawing and the interior of the body is to the left in the drawing. If a pressure is mechanically exerted from the outside through the skin on the base 18, depending on the force, the base 18 is deformed/curved inwardly and the shaft 7 is pushed downward to the cover 20. As a result, the gap 19 is closed, the shaft 7 presses against part 9 and thus lifts the entire rotor up from the base 18. The elastic bias of the base 18 is overcome and the friction forces at the position 8 are thereby neutralized. Then, at the position 8, a gap is created and the rotor can rotate freely. If the external load is removed again, the outer base 18 returns to its initial position and generates the elastic bias between contact point 17 and contact point 18. The rotor is again clamped in the housing, and no rotation is possible.

The rotor 1 has a cam disc 13.

FIG. 2 shows the rotor 1 in the minimum position. By rotating the rotor by approximately 300 degrees, the spring 10 at the contact point 21 and under the control of the cam 13 is moved into its maximum position, so that the resulting opening pressure now becomes maximum. The vertical difference between the minimum and maximum spring bias of part 4 or 10 is approximately 0.7 to 0.8 mm. In concrete terms, however, this amount depends on the dimension of the titanium wire 10 selected.

The two magnets 2 and 3 are arranged so that an externally applied magnetic field can produce a maximum torque.

In other words, the distance between the two magnets in the exemplary embodiment is 7 mm. In another exemplary embodiment it is 8 mm and in additional exemplary embodiments it can be up to 20 mm. In concrete terms, this difference is determined on the basis of the external dimensions of the housing. The circular housing preferably has a diameter of 14 mm, in other exemplary embodiments a diameter of up to 19 mm and in additional exemplary embodiments diameters of up to 31 mm, and is shaped ergonomically, so that on one hand the position of the valve can be easily felt from outside, while on the other hand the tissue that lies on top of the valve is not damaged.

Sharp edges are thereby eliminated.

The rotor has a tip 22 which is illustrated in FIG. 2. This tip strikes the stop 14 at the minimum value and the stop 23 at the maximum value. In the illustrated exemplary embodiment, the presence of this stop prevents any sudden change between the maximum and minimum settings and ensures that it is easy to distinguish between them at all times. In other exemplary embodiments, a transition can also be provided.

The shaft 15 preferably has a diameter of 0.3 mm and can optionally have a tip on the top and bottom, to minimize the bearing forces. As a result of the construction described above, the rotor 1 can rotate only if the base 18 in the drawing is pressed to the left and the rotor 1 can thereby rotate freely. In this position, a specific magnetic field must also be located externally to securely initiate a rotation. If the load is then removed from the base, the position of the rotor is fixed by elastic clamping. If a pressure differential that is greater than the opening pressure of the valve then occurs between the inlet 11 and the outlet 12, the ball 5 is pushed out of its valve seat against the leaf spring and moved toward the rotor. It thereby becomes possible for the liquor to flow through the valve to the drain and any further increase in pressure is prevented. The actual valve characteristic is defined by the rotational position of the rotor 1 and/or by the resulting position of the contact point 21 on the spiral or on the cam disc 13. By a targeted modification of the shape of the curve, in other exemplary embodiments a non-linear curve of the opening characteristic can also be achieved as a function of the angle of rotation of the rotor 1.

The rotor is preferably fabricated so that in all starting positions of the rotor, a rotation of 10 degrees in either direction results in the same variation of the opening pressure of the valve. The location of the magnets 2 and 3 as far apart from each other as possible has the advantage that the lowest possible magnetic forces can achieve the highest possible adjustment moments. The neodymium magnets used in this case have a cylindrical shape with a diameter of 1 mm and a height of approximately 1.2 mm.

The fabrication of the housing and the rotor and the fabrication of the other components from titanium has the advantage that an ideal bearing play with exact fits can be achieved, and undesirable play and undesirably high friction can be systematically avoided. The shaft 7, for example, preferably has a diameter of 1 mm, and the play at position 24 between the shaft 7 and the rotor 1 is preferably tolerated by a close adjustment of the play. A play adjustment of this type is provided for the bearing of the shaft 15 in the valve housing. This shaft 15 is mounted like a door hinge in the valve housing and makes possible an almost completely friction-free rotation of the leaf spring 4 in the context of the opening and closing of the valve. The height of the valve is approximately 4.5 mm. Significantly lower heights are not necessarily desirable, if even possible, because it should not be too difficult to locate the valve by palpation.

Figure 3:
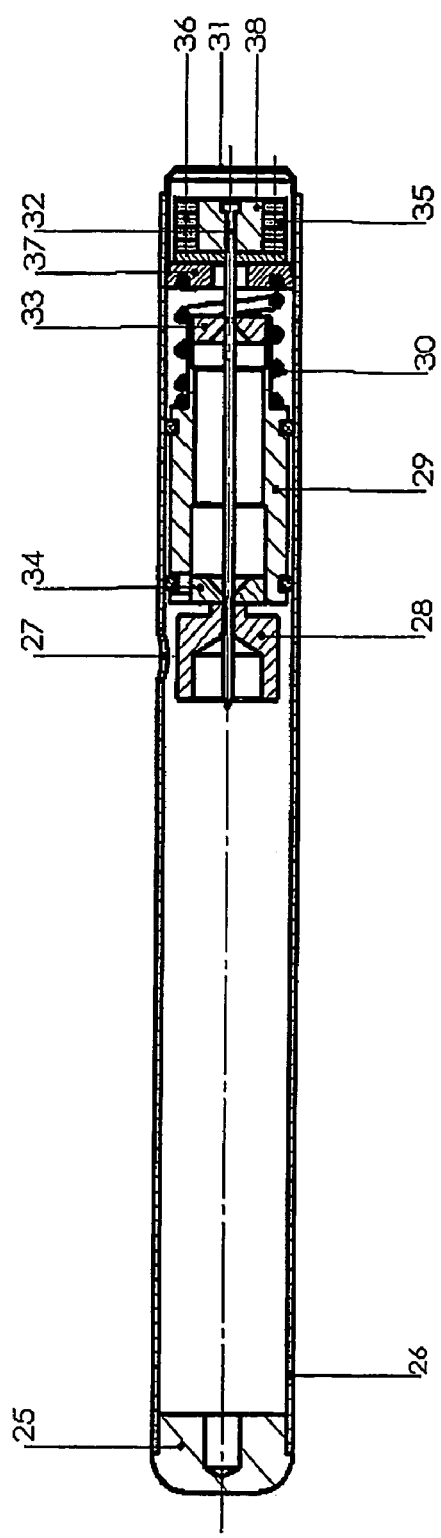
FIG. 3 shows an adjustment pin for a hydrocephalus valve arrangement according to at least one possible embodiment.

Special adjustment pins have been developed for the adjustment of the valve. One exemplary embodiment of such a pin is illustrated in FIG. 3. The illustration also contains an enlargement with respect to the exemplary embodiment, but less than in FIGS. 1 and 2. To arrive at the correct relationship between the dimensions of the valve and the dimensions of the pin as the adjustment device, it is a good idea to look at the pin in an appropriate enlargement together with the valve.

In the life-size drawing, all the details are so small that they are no longer clearly visible.

A thin-walled small tube 26 with a diameter of approximately 12 mm is closed on one end by a plug 25. On the other side, a measurement mechanism mounted on a needle bearing is installed. The latter mechanism includes: a measurement drum 28, on the surface of which a graduated scale is applied, and which is connected with the shaft 32 which is mounted in the bearing bushing at the points 34 and 33. The bearing bushing 29 is introduced into the small tube 26 so that it cannot be displaced or rotated. On the side of the small tube that is not closed, a movable cap is introduced into the small tube, and is pushed outward by a spring force. The spring 30 is supported on the bearing bushing 29 and presses the ring 37 against the cap 31. The cylinder 38 is connected with the needle 32.

Magnets 35 and 36 are introduced into the cylinder 38. The external pole on the one magnet is negative and on the other magnet it is positive. The distance between the magnets is approximately equal to the distance between the magnets inside the valve, likewise the diameter.

The shaft of the rotor and of the cylinder 38 cannot be rotated by the cap 31 and the spring 30, as long as the cap is not pressed opposite to the spring force on the bearing bushing. Only if the pin is pressed above the valve against the patient's head, and thus the cap 31 is pushed into the housing, is a rotation of the rotor and scale drum, as well as the magnet cylinder, possible. The pin must be pressed against the patient's head so that the window 27 can rotate by 90 degrees in relation to the body axis. This measure ensures that the valve pin and the valve itself have the same directional orientation. If the cap is then pressed above the valve in front of the patient's head, the position of the rotor inside the pin follows the position of the rotor inside the valve, because the valve rotor cannot vary in its position on account of the elastic clamping, although on account of the precision needle bearing at the points 33 and 34, the pin rotor can adjust by rotating to match the position of the valve-side rotor. The corresponding pressure setting of the valve can now be read easily in the window 27. This construction guarantees a reliable measurement that can easily be repeated at any time. By fixing the measurement only a few tenths of a millimeter away from the head, it is no longer possible to rotate the pin or to remove it from the patient's head. The measurement result is "frozen" immediately.

Figure 4:
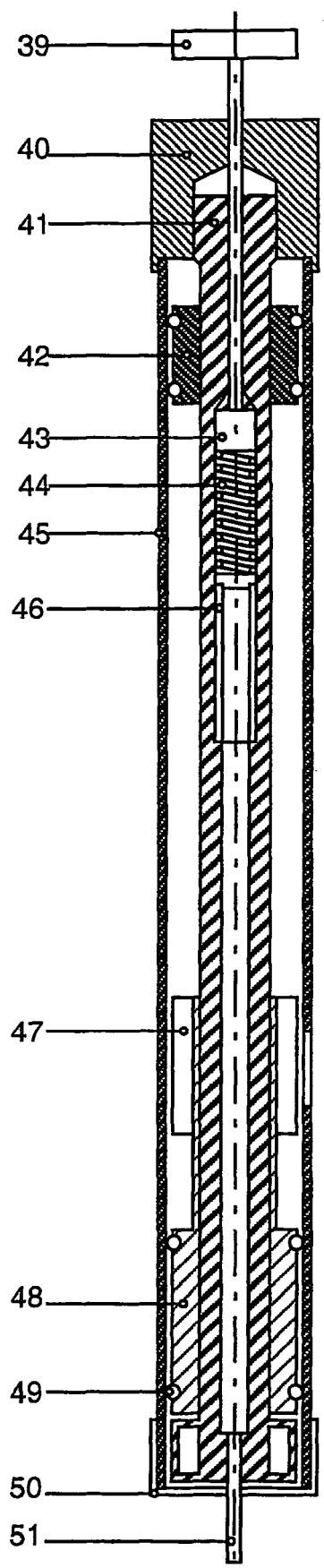
FIG. 4 shows another adjustment pin for a hydrocephalus valve arrangement according to at least one possible embodiment.

FIG. 4 shows an additional exemplary embodiment of an adjustment pin. The external dimensions are approximately the same as those of an ordinary ball-point pen, i.e. the small tube has an outside diameter of preferably 12 mm and a length of approximately 10 cm. The adjustment wheel 40 is permanently affixed to the shaft 41. A rotation of this wheel causes a rotation of the shaft. On the lower end of the shaft 40, two cylindrical magnets 50 are introduced into the shaft. As in the valve, these magnets have different poles. The south pole on one of the magnets is on the bottom, and on the other magnet the north pole is on the top. The position of the two magnets on the shaft corresponds to the position of the graduated scale that appears on part 47. This graduated scale is also permanently connected with the shaft.

The bushing 48 acts as a bearing for the shaft 41. The bushing is introduced through O-rings by which the bushing is fixed in the sleeve 45. A second bearing bushing is attached on the upper portion of the pin, part 42. Here, too, the shaft 43 is fixed in the form of a simple bearing in the bushing 42. The adjustment pin contains two different springs: a strong spring 44 and an extremely weak spring 46. By pressing on the button 39 the shaft 43, which has a piston-like expanded portion in its lower region, is displaced downward against the spring force 44. The shaft 51 is thereby pushed downward against the spring force of the significantly weaker spring 46. The spring 46 is therefore significantly compressed, while on the other hand the spring 44 is only slightly compressed. The force of the spring 44 is transmitted by the shaft 51 to its lower tip, which in this application is designed to exert the force on the valve that is to be uncoupled. The diameter of the shaft at the tip should preferably be approximately 3 mm, and the bottom end should be rounded in a dome shape. The cap 51 that is attached to the lower end of the pin protects the bearing as well as the magnets 50 that are installed in the shaft 41. The position of the magnets can be read through the window 53 on the graduated scale of the scale drum 47. The construction taught by the invention makes it possible to keep the construction of the adjustment unit small without negatively affecting the safety and reliability of the adjustment.

It therefore becomes possible for the first time to realize such adjustment pins. The construction makes it possible to place the magnets as close as possible to the patient's skin. A precise and accurate adjustment can be made by the simultaneous application of pressure to the valve housing.

Figure 5:
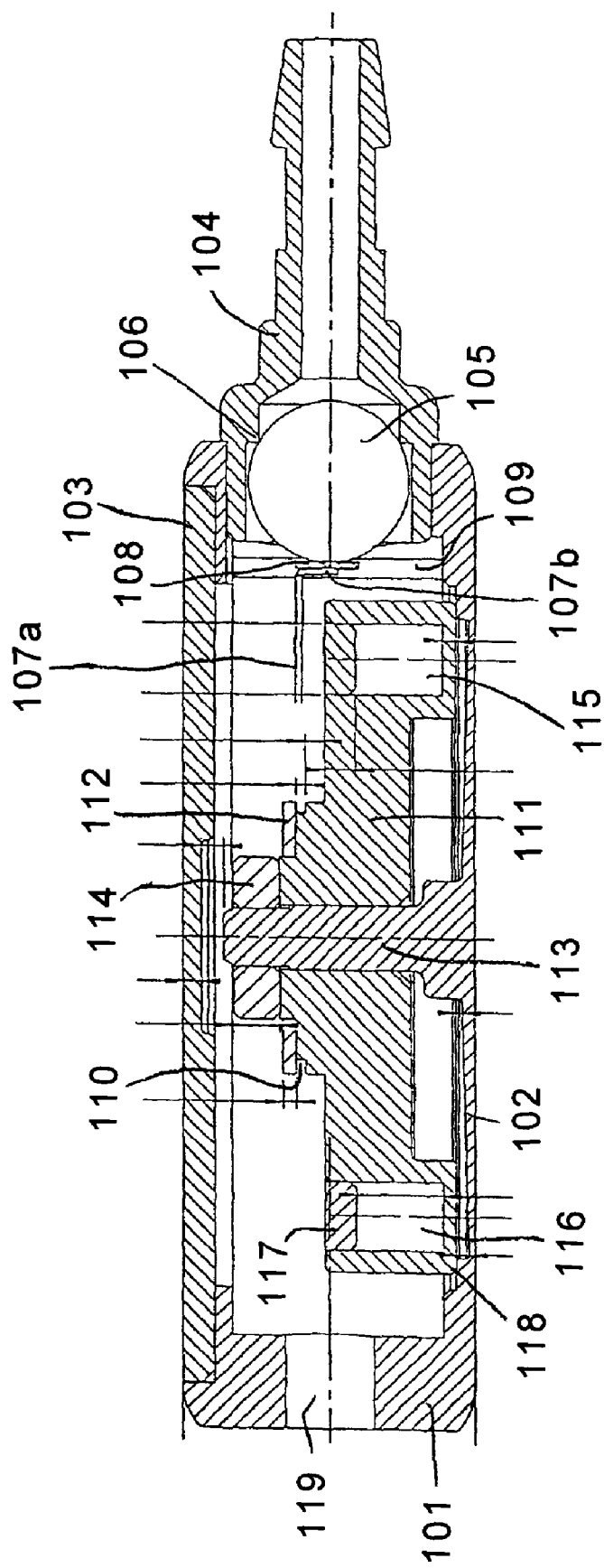
FIG. 5 shows a cross-sectional view of a hydrocephalus valve arrangement according to at least one possible embodiment.
Figures 6, 7:
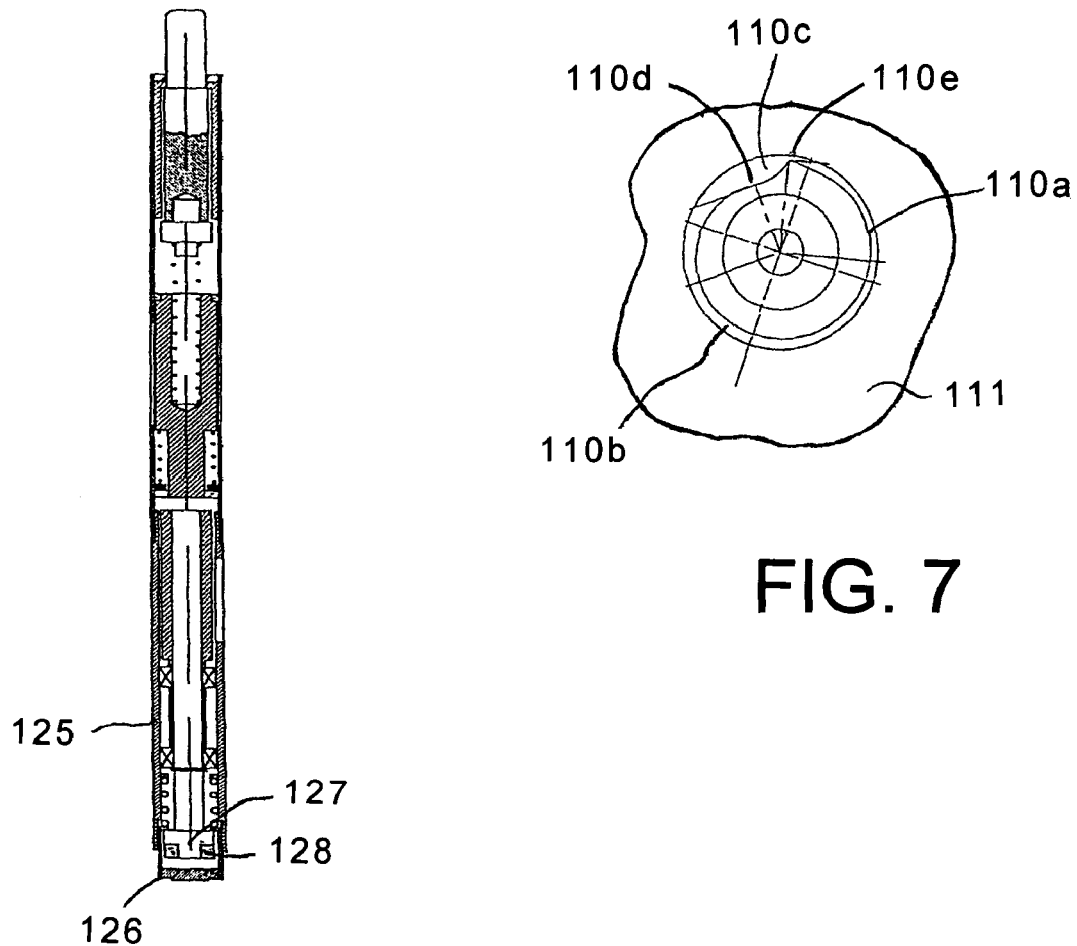
FIG. 6 shows an adjustment device for a hydrocephalus valve arrangement according to at least one possible embodiment.
FIG. 7 shows a cylindrical molding of a hydrocephalus valve arrangement according to at least one possible embodiment.

FIGS. 5 to 7 show additional exemplary embodiments. FIG. 5 also shows a section through a valve as claimed by the invention in an enlarged illustration. The actual diameter in the exemplary embodiment is less than 20 mm and the thickness is less than 6 mm. The dimensions in other exemplary embodiments can be even smaller.

The valve includes a steel housing that consists of a cylindrical ring 101, a molded steel base 102 and a cover 103. The ring 101 is provided on the inflow side with an insert 104. In the insert there is a valve ball 105 which seals a valve bore 106. The valve ball 105 is pressed against the valve bore 106 by a wire-shaped spring. The spring is realized in the form of a two-armed lever with one long lever arm 107a and one small/short lever arm 10b.

The two lever arms 107a and 107b are at an acute angle to each other because the section runs through the center of the valve and because the spring is illustrated in the area that lies behind the plane of the section in the figure, and because the free end of the lever arm 107a extends into the area that is not illustrated that lies in front of the plane of the section, and because the drawing of the short lever arm 107b indicates a path that is exactly perpendicular to the plane of the drawing and the plane of the section.

Other angles are possible in other exemplary embodiments.

The spring is soldered to a pin 109 between the two lever arms 107a and 107b. The pin is located to one side of the valve ball 105 and has two sharp ends, with which it is pivotably mounted in the cylindrical ring 101.

Attached to the short lever arm 107b is a plate 108, with which the spring presses against the valve ball 105. The more pressure is applied by the spring, the greater becomes the valve resistance against the entry of liquor. The less pressure is applied by the spring, the less the valve resistance against the entry of liquor.

The penetrating liquor travels via a discharge opening and an implanted hose (not shown) into the patient's abdomen.

The long lever arm 107a extends in the exemplary embodiment to the middle of the cylindrical ring 101, where it slides along a curved path 110. The curved path is located in a slot, where it forms the base of the slot and is a component of a cylindrical molding 111 in the form of an adjustment plate, which is called simply a "molding" below. The one lateral boundary of the slot is formed by the cylindrical molding 111.

The other lateral molding of the slot is formed by a disc 112. FIG. 6 shows details. FIG. 6 shows a detail of the molding 111 with the curved path 110a and the lateral boundary 110b, which is formed by the molding 111 itself.

The curved path 110a has a beginning 110d and an end 110e. By rotating the molding 111 clockwise, the lever arm 107a is pushed to the left in the plane of FIG. 6. The spring tension is thereby increased, and there is a greater pressure on the valve ball 105.

When the molding 111 moves counterclockwise, the spring tension is reduced and the pressure on the valve ball 105 is reduced.

The disc 112 sits on a shoulder of the molding 112, where it is fastened in a manner not shown.

In addition, there is a connection between the end 110e and the beginning 110d of the curved path, so that the molding, when it reaches the end 110e, can simply continue to rotate, so that it comes back to the beginning 110d.

The molding 111 can move rotationally on a bearing pin 112 where it is secured with a ring 114.

In the exemplary embodiment, the molding 111 has bores 115 and 116 for permanent magnets that are diametrically opposite each other. The permanent magnets are realized in the form of pin magnets. Their diameter in the exemplary embodiment is 2 mm. The magnets are held in the recesses 115 and 116 by covers 117. The magnets are at a small distance from the steel base 102 of the valve housing.

To set the valve pressure, the molding 111 is rotated and the spring pressure is increased or decreased as appropriate. The valve pressure is set by rotating the molding.

To rotate the molding, there is an adjustment device of the type illustrated in FIG. 7.

The adjustment device includes a housing 125 with a cap 126, with which the adjustment device is placed on the valve.

In the housing 125 is a head 127 with two pin magnets 128. The pin magnets 128 are at the same distance from each other as the magnets of the molding 111, although they are arranged so that when the adjustment device is placed on the valve, they have different poles from the magnets of the molding 111. The magnets are thereby attracted to each other and the molding 111 follows a rotation or a pivoting movement of the adjustment device with a rotation or pivoting movement in the same direction.

The accurate positioning of the adjustment device is advantageously facilitated. All it takes is slight contact, and the attractive force of the magnets guides the adjustment device into the correct position.

The pressure is then increased to cause a slight deformation of the valve housing. The housing bottom or housing cover is thereby elastically deformed. To facilitate the deformation, the base 2 is provided with a deformation thickness. The deformation thickness in the exemplary embodiment is 0.2 mm.

The consequence of the deformation is that the molding 111 lifts up from the corresponding friction surfaces. The friction is neutralized. The molding can then be easily rotated or pivoted.

To take the deformation claimed by the invention into consideration, a corresponding clearance is provided in the housing. For that purpose, a depression for the ring 114 and the bolt 113 is provided in the cover 103.

For the application of pressure, a mechanism similar to a ball-point pen is provided in the adjustment device. The mechanism effects a resilient application of pressure. The spring protects the valve housing from excessive deformation.

The magnets can thereby be arrested by the ball-point-pen mechanism in the position necessary for the adjustment in the cap 126, or can be retracted again after the adjustment has been made. When the adjustment device is removed, that prevents any undesirable further adjustment caused by unintentional or unskilled movement of the adjustment device.

In the exemplary embodiment, the pressure applied to the head 127 in the cap 126 is selected by a corresponding design of the spring system so that a rotation of the housing 125 by the treating physician leads to an accompanying rotation of the head 127.

In other exemplary embodiments, alternatively or additionally, there is a guidance of the head 127 which, by itself or together with an application of pressure, causes the above-mentioned tracking movement of the head 127 when the housing 126 is rotated.

For the guidance, in one exemplary embodiment a tongue-and-groove connection is provided, which makes axial mobility possible, but results in a non-rotational arrangement in the peripheral direction.

Figure 1A:
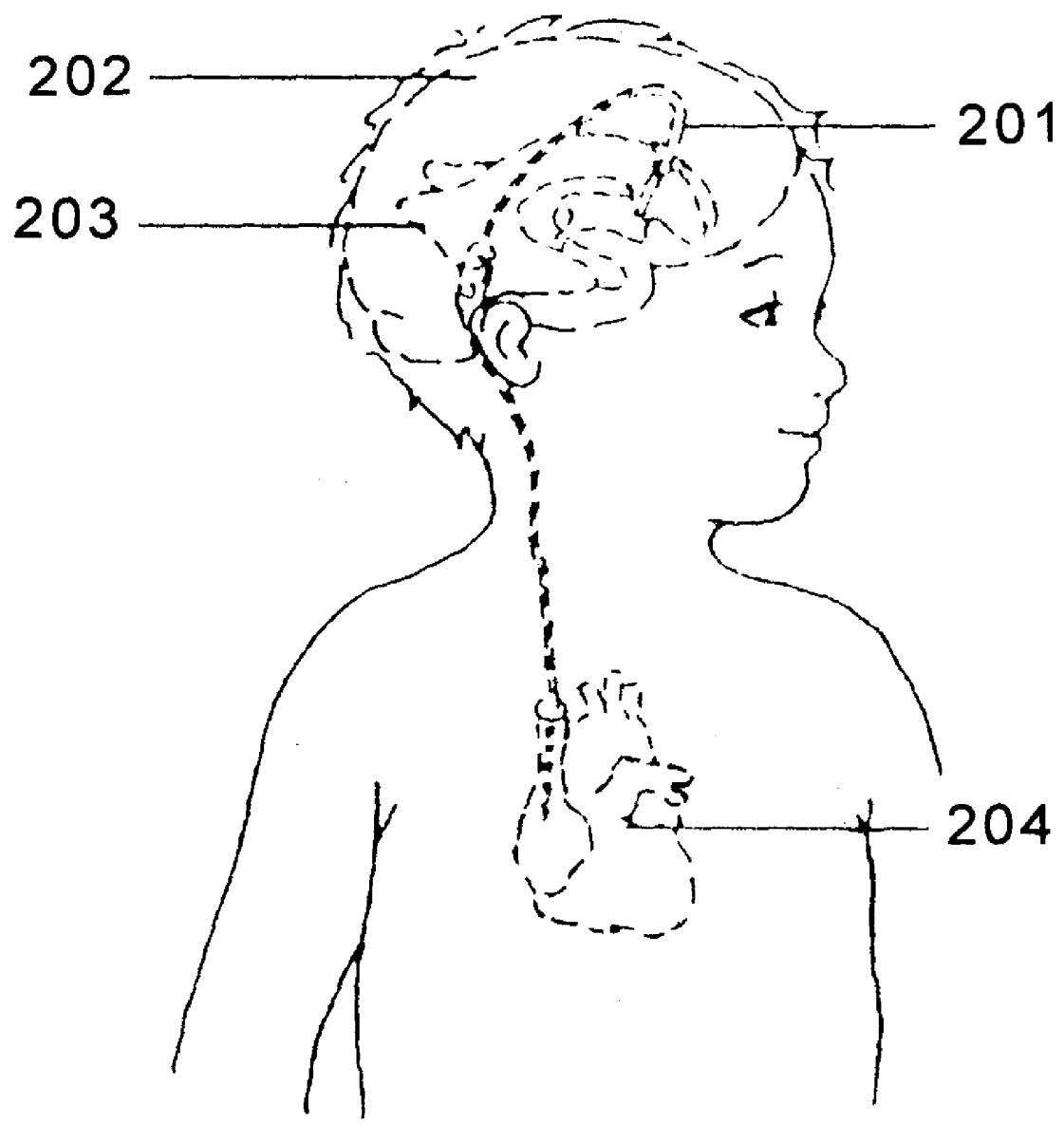
FIG. 1A shows an example of a hydrocephalus treatment device connected to a patient.

FIG. 1A shows an example of a hydrocephalus treatment device connected to a patient. The device comprises a ventriculo-atrial (VA) shunt 201. The VA shunt 201 moves cerebrospinal fluid from the ventricles 203, or spaces in the brain 202, into the atrium, or top chamber, of the heart 204 through a vein in the neck.

Figure 1B:
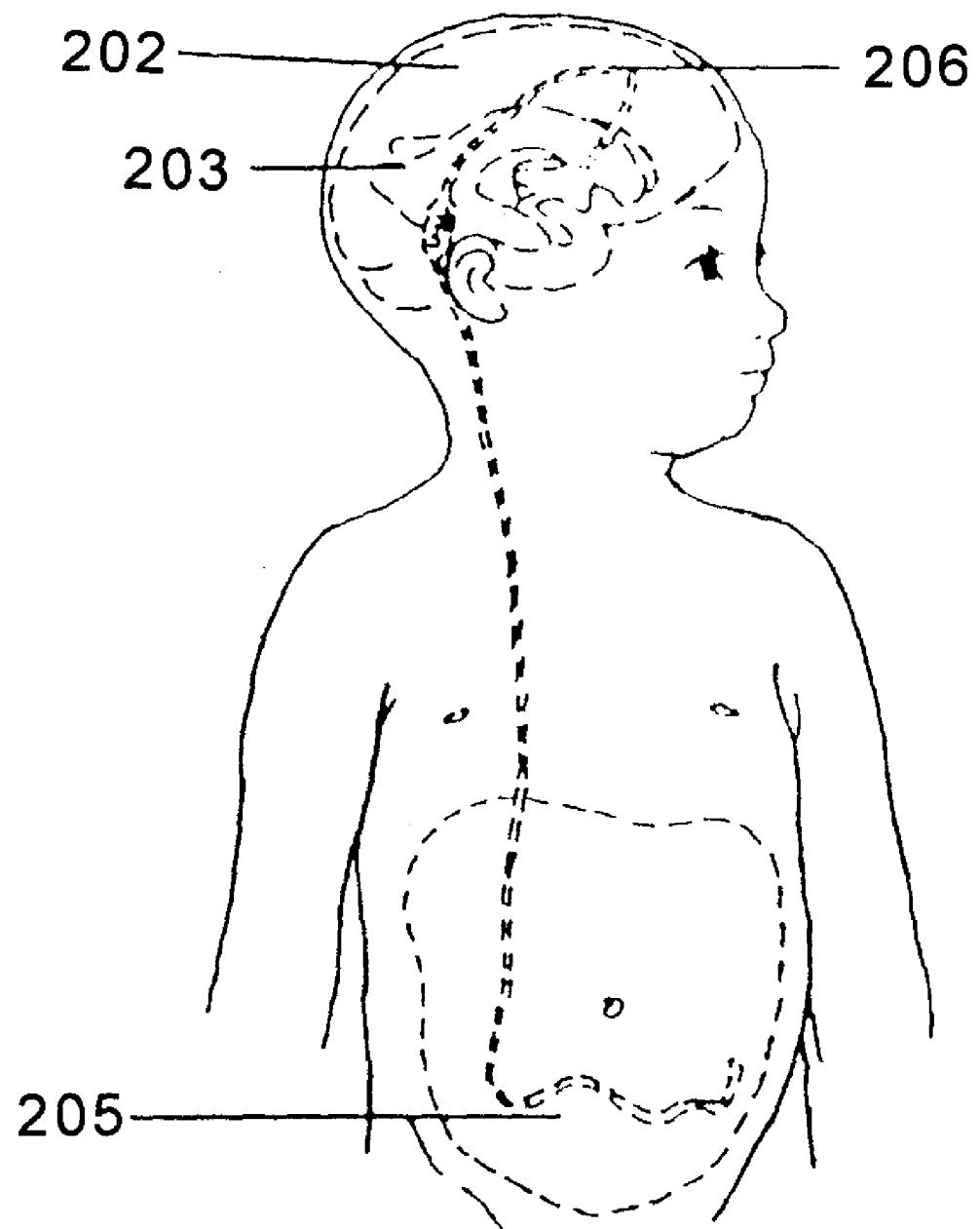
FIG. 1B shows an example of a hydrocephalus treatment device connected to a patient.

FIG. 1B shows an example of a hydrocephalus treatment device connected to a patient. The device comprises a ventriculo-peritoneal (VP) shunt 206. The VP shunt moves cerebrospinal fluid from the ventricles 203, or spaces in the brain 202, to a space in the peritoneal cavity inside the abdominal cavity 205.

Some examples of methods or devices for treating hydrocephalus which may possibly be utilized or adapted for use in at least one possible embodiment may possibly be found in the following U.S. Pat. No. 6,882,876, entitled "Diagnosis of normal pressure hydrocephalus by automated processing of MR images;" U.S. Pat. No. 6,840,917, entitled "Implantable subcutaneous valve for the treatment of hydrocephalus, and adjusting devices therefor;" U.S. Pat. No. 6,540,727, entitled "Process for treating a patient with hydrocephalus utilizing an external medical draining system;" U.S. Pat. No. 6,283,934, entitled "Device for the treatment of hydrocephalus;" U.S. Pat. No. 6,193,682, entitled "Low profile neonatal hydrocephalus device and methods;" U.S. Pat. No. 6,146,352, entitled "Implantable drainage valve for the treatment of hydrocephalus;" U.S. Pat. No. 5,928,182, entitled "Pediatric programmable hydrocephalus valve;" U.S. Pat. No. 5,843,013, entitled "Valve for the treatment of hydrocephalus;" U.S. Pat. No. 5,728,061, entitled "Device and method for treating hydrocephalus;" U.S. Pat. No. 5,368,556, entitled "Implantable drainage valve for the treatment of hydrocephalus;" U.S. Pat. No. 5,207,684, entitled "Sheath for shunt placement for hydrocephalus;" U.S. Pat. No. 5,069,663, entitled "Hydrocephalus valve;" U.S. Pat. No. 5,000,731, entitled "Shunting device adopted in the intracranial shunting surgical operation for the treatment of hydrocephalus;" U.S. Pat. No. 4,787,887, entitled "Ventricular by-pass valve for draining the cephalorachidian liquid in the hydrocephalus;" U.S. Pat. No. 4,741,730, entitled "Hydrocephalus shunt with in-line filter;" U.S. Pat. No. 4,673,384, entitled "Valve for the treatment of hydrocephalus;" U.S. Pat. No. 4,588,085, entitled "Sterile air feedthrough packaging system for testing hydrocephalus shunt valves;" U.S. Pat. No. 4,443,214, entitled "Valve for the treatment of hydrocephalus;" U.S. Pat. No. 4,432,853, entitled "Method of making an ion beam sputter-etched ventricular catheter for hydrocephalus shunt;" U.S. Pat. No. 4,377,169, entitled "Ion beam sputter-etched ventricular catheter for hydrocephalus shunt;" and U.S. Pat. No. 4,375,816, entitled "Catheters for shunting systems for the treatment of hydrocephalus."

Some examples of medical valves which may possible be utilized or adapted for use may possibly be found in the following U.S. Pat. No. 6,892,998, entitled "Medical valve and method of assembling the same;" U.S. Pat. No. 6,883,778, entitled "Apparatus for reducing fluid drawback through a medical valve;" U.S. Pat. No. 6,875,198, entitled "Surgical suction regulator valve;" U.S. Pat. No. 6,869,426, entitled "Anti-drawback medical valve;" U.S. Pat. No. 6,837,852, entitled "Control valve for suction device for surgical applications;" U.S. Pat. No. 6,805,688, entitled "Method and device for use in micro-invasive surgical procedures, and guide catheter and valve unit for a device for use in micro-invasive surgical procedures;" U.S. Pat. No. 6,802,490, entitled "Needle free medical connector with expanded valve mechanism and method of fluid flow control;" U.S. Pat. No. 6,790,237, entitled "Medical stent with a valve and related methods of manufacturing;" U.S. Pat. No. 6,767,340, entitled "Sealing valve assembly for medical products;" U.S. Pat. No. 6,764,494, entitled "Device for removal of an aorta valve at a human heart in course of a minimal surgical operation;" U.S. Pat. No. 6,755,391, entitled "Anti-drawback medical valve;" U.S. Pat. No. 6,712,791, entitled "Splittable medical valve;" U.S. Pat. No. 6,706,022, entitled "Needleless medical connector with expandable valve mechanism;" U.S. Pat. No.

6,695,817, entitled "Medical valve with positive flow characteristics;" U.S. Pat. No. 6,682,509, entitled "Medical valve and method of use;" U.S. Pat. No. 6,669,673, entitled "Medical valve;" U.S. Pat. No. 6,648,017, entitled "Valve arrangement for a medical apparatus;" U.S. Pat. No. 6,641,559, entitled "Buret with foot valve for medical infusion equipment;" U.S. Pat. No. 6,635,044, entitled "Medical valve with fluid escape space;" U.S. Pat. No. RE38,145, entitled "Luer-receiving medical valve;" U.S. Pat. No. 6,572,592, entitled "Medical valve and method of use;" U.S. Pat. No. 6,537,258, entitled "Valve for medical infusion lines and the like;" U.S. Pat. No. 6,506,197, entitled "Surgical method for affixing a valve to a heart using a looped suture combination;" U.S. Pat. No. 6,481,462, entitled "Medical flush valve;" U.S. Pat. No. 6,447,473, entitled "Medical suction valve;" U.S. Pat. No. 6,436,067, entitled "Powered surgical handpiece with suction conduit including a stepped valve to regulate flow through the suction conduit;" and U.S. Pat. No. 6,427,691, entitled "Medical valve."

Some examples of shunt valves which may possibly be utilized or adapted for use in at least one possible embodiment may possibly be found in the following U.S. Pat. No. 6,666,208, entitled "Set for inserting a shunt valve into a shunt between the oesophagus and the trachea;" U.S. Pat. No. 6,358,222, entitled "Shunt valve;" U.S. Pat. No. 6,289,990, entitled "Production tubing shunt valve;" U.S. Pat. No. 6,255,806, entitled "Supply device for power supply to an electronic unit in a semiconductor valve in a shunt-connected thyristor-switched capacitor;" U.S. Pat. No. 6,029,703, entitled "Pressure solenoid control valve with flux shunt;" U.S. Pat. No. 6,007,511, entitled "Shunt valve and therapeutic delivery system for treatment of glaucoma and methods and apparatus for its installation;" U.S. Pat. No. 5,935,095, entitled "External slot valve for controlling blood flow through the outlet of a shunt of a cardiopulmonary bypass pump;" U.S. Pat. No. 5,304,114, entitled "Shunt valve system;" U.S. Pat. No. 5,042,974, entitled "Shunt valve;" U.S. Pat. No. 4,867,740, entitled "Multiple-membrane flow control valve and implantable shunt system;" U.S. Pat. No. 4,772,257, entitled "External programmer for magnetically-adjustable cerebrospinal fluid shunt valve;" U.S. Pat. No. 4,595,390, entitled "Magnetically-adjustable cerebrospinal fluid shunt valve;" U.S. Pat. No. 4,553,956, entitled "Shunt valve and method of use;" U.S. Pat. No. 4,551,128, entitled "Cerebrospinal fluid shunt valve;" U.S. Pat. No. 4,475,899, entitled "Shunt valve and method of use;" U.S. Pat. No. 4,387,715, entitled "Shunt valve;" U.S. Pat. No. 4,332,255, entitled "Shunt valve;" U.S. Pat. No. 4,094,145, entitled "Underspeed actuator for a hydrostatic transmission having a shunt valve;" U.S. Pat. No. 3,998,222, entitled "Subcutaneous arterio-venous shunt with valve;" U.S. Pat. No. 3,991,768, entitled "Shunt system resistant to overdrainage and siphoning and valve therefor;" and U.S. Pat. No. 3,985,140, entitled "Dual pressure valve for use in ventricular shunt system."

The invention claimed is:

1. An adjustable hydrocephalus pressure control arrangement to control the pressure of the fluid in the cranium of a hydrocephalus patient, said pressure control arrangement comprising:

a housing comprising an inlet opening for permitting entry of fluid into said housing and an outlet opening for permitting exit of fluid from said housing;
said housing comprising a flexible housing wall;
said flexible housing wall comprising an inside surface and an outside surface;
said inside surface of said flexible housing wall comprising a flat frictional surface;
a valve arrangement being disposed in said housing and being configured and disposed to control flow of fluid through said housing, said valve arrangement comprising:
a ball structure being disposed adjacent said inlet opening;
a spring structure being configured and disposed to apply pressure to said ball structure to control flow of fluid through said inlet opening and into said housing;
a rotor being connected to said spring structure to adjust said spring structure to increase or decrease pressure on said ball structure;
said rotor comprising magnets being configured and disposed to be acted on by an outside magnetic force to rotate said rotor in a clockwise or counterclockwise manner to adjust said spring structure;
said rotor comprising a flat frictional surface being configured and disposed to make frictional contact with said flat frictional surface of said inside surface of said flexible housing wall to thus hold said rotor stationary and minimize unintentional movement of said rotor;
a rotor support structure being configured and disposed to project from said inside surface of said flexible housing wall and through a central portion of said rotor; and
said rotor being disposed to be rotated about said rotor support structure, and being operatively connected to said rotor support structure; and
said flexible housing wall being configured, upon application of a pressing force on said outside surface of said flexible housing wall, to be bent inwardly to move said rotor support structure axially to thus displace said rotor operatively connected to said rotor support structure out of contact with and a distance away from said flat frictional surface of said inside surface of said flexible housing wall to permit rotation of said rotor; and
said flexible housing wall being configured, upon absence of a pressing force on said outside surface of said flexible housing wall, to be bent outwardly to move said rotor support structure axially to thus displace said rotor operatively connected to said rotor support structure into contact with and biased against said flat frictional surface of said inside surface of said flexible housing wall.

2. The pressure control arrangement according to claim 1, wherein:

said flexible housing wall comprises an elastic, resilient side wall configured to resume its initial, outwardly-bent shape upon termination of a pressing force thereon;
said rotor is flat and plate-shaped and comprises a projecting lip disposed about a substantial portion of the periphery thereof; and
said flat frictional surface of said rotor is disposed on said projecting lip.

3. The pressure control arrangement according to claim 2, wherein:

said flexible side wall has a thickness of one of: up to 0.5 mm and up to 0.2 mm;
said flexible side wall is configured to be deformed for the frictional contact up to a dimension that is one of: equal to twice the thickness of said flexible side wall, and up to 0.1 mm;
at least one of said housing and said flexible side wall comprises one of: a metal, titanium, and a titanium alloy; and
said spring structure comprises a pivotable spring bar, whereby the pivoting plane of said spring bar runs parallel to the plane of motion of said rotor.

4. The pressure control arrangement according to claim 3, wherein:

said valve arrangement having a valve characteristic of variable pressure and flow generated by a metal wire or plate, the cross section of which is one of: round and rectangular, and the thickness of which is up to one of: 0.5 mm, 0.3 mm, and 0.2 mm the spring bar comprises a two-armed lever arm, the one lever arm of which is mechanically connected with the adjustment plate and the other lever arm of which is mechanically connected with the ball structure;

the spring bar is flexibly mounted and the mechanical connection is formed by at least one of: one lever arm being configured to slide against a cam plate of said rotor, and the other lever arm being configured to slide against said ball structure;

said two lever arms enclose an angle between them that is one of: less than 180 degrees and less than 90 degrees;

said lever arms are one of: straight and curved;

said cam plate of said rotor has one of (a) and (b): (a) a spiral shape so that when said rotor is rotated, the spring tension is varied one of: progressively and uniformly, and (b) a non-uniform profile so that the spring tension is varied unevenly; and one of (c) and (d):

(c) a trajectory of said cam disc extends over less than 360 degrees and the ends of the trajectory are limited by stops, so that the adjustment thereof results in a back-and-forth pivoting movement of said rotor; and (d) a trajectory of said cam disc extends over a peripheral angle of at least 300 degrees, and between the two ends of the spiral-shaped part a transition is provided, so that the spring, after it reaches one extreme position, moves into the other extreme position as a result of a progressive rotation of the part in the same direction with an adjustment travel of the trajectory from one of: 0.1 to 2 mm and 0.5 to 0.9 mm, whereby the actual gradient of the trajectory is determined on one hand by the actual surface area on the valve seat and on the other hand by the requirements regarding the adjustment ranges, such as toward an increasingly greater delta-p at high setting pressures.

5. The pressure control arrangement according to claim 4, wherein:

said two-armed lever spring realized comprises a pivoting bearing held with a pin that is engaged in each end in a recess in the housing;

the pin is provided with tips on its ends and pivots on the tips in the recesses;

the pin is welded or soldered to the spring;

the pin has a diameter of up to one of: 3 mm, 2 mm, and 1 mm; and said spring bar is configured to contact a portion of the surface of said ball structure.

6. The pressure control arrangement according to claim 5, wherein:

the spring makes a transition on the valve ball into a sheet;

the sheet is welded or soldered on;

each lever of said two-armed lever springs have a different cross section and comprise a rotor-side arm comprising a spring wire and a ball-side arm comprising a leaf spring;

the welded connections are laser-welded connections;

the valve arrangement has a ring-shaped housing which is provided with a base and a top, whereby a) at least the base or the cover is detachable and b) a bearing pin for the part is provided on the base or on the cover, c) in the housing ring a feed opening and a discharge opening is provided, whereby at least in one of the openings a valve ball sits which is held in the function position by the spring;

the housing has at least one of (i) and (ii): (i) an outside diameter up to one of: 31 mm and 20 mm, and (ii) a height up to one of: 10 mm and 6 mm;

the flexible side wall carries a pivot on which the rotor is rotationally mounted;

the rotor is braced against the flexible side wall for the deformation of the flexible side wall on its pivot;

the braced housing wall, for further deformation, has some freedom of movement for penetration into the rotor; and the rotor, after the stop is released, has freedom of movement with respect to the surrounding housing for the adjustment movement.

7. A method of controlling the pressure of the fluid in the cranium of a hydrocephalus patient using an adjustable hydrocephalus pressure control arrangement according to claim 1, said method comprising the steps of:

applying a pressing force on said outside surface of said flexible housing wall to bend said flexible side wall inwardly to move said rotor support structure axially and displacing said rotor operatively connected to said rotor support structure out of contact with and a distance away from said flat frictional surface of said inside surface of said flexible housing wall;

applying a magnetic force to said magnets in said rotor and rotating said rotor to a desired position corresponding to a desired pressure on said valve body;

terminating applying the magnetic force to said magnets upon said rotor being rotated to the desired position; and terminating applying said pressing force on said outside surface to permit said flexible housing wall to bend outwardly to move said rotor support structure axially to thus displace said rotor operatively connected to said rotor support structure into contact with and biased against said flexible housing wall to thus increase the frictional contact between said flat frictional surface of said rotor and said flat frictional surface of said inside surface of said flexible side wall, and thus securing said rotor in the desired position to maintain the desired pressure on said valve body.

8. The pressure control arrangement according to claim 1, in combination with an external adjustment device for applying a pressing force to said flexible housing wall and applying a magnetic force to said magnets of said rotor, wherein:

said external adjustment device comprises magnets, wherein said magnets of said external adjustment device and said magnets of said rotor face each other with opposite poles, so that a torque from said external adjustment device is transmitted to rotor; and said magnets have a diameter of one of: up to 3 mm and up to 1 mm, and a height of one of: up to 5 mm and up to 2 mm;

said magnets of said external adjustment device are at a distance from each other that differs from the distance between said magnets of said rotor by one of: a maximum of 3 mm and a maximum of 1 mm;

said magnets are at a maximum distance from each other of one of: 20 mm, 10 mm, and 8 mm; and said magnets of said external adjustment device in the vertical position of said external adjustment device can be moved up and down therein.

9. The combination according to claim 8, wherein:
said adjustment device is provided with a cap that can be placed on the patient's skin over the implanted pressure control arrangement;
the force provided for the elastic deformation of the housing is applied with the external adjustment device by means of an interposed spring element in the form of a power limiter;
said external adjustment device is provided with a measuring device for the adjustment movement;
said measuring device comprises at least one of: a pressure measuring device and a rotation measuring device;
said external adjustment device adjusts freely to the magnet position in the valve arrangement and the rotational position of the magnets can be read externally;
said external adjustment device comprises a reading window for reading the pressure.

10. A method of controlling the pressure of the fluid in the cranium of a hydrocephalus patient using an adjustable hydrocephalus pressure control arrangement in combination with an external adjustment device according to claim 9, said method comprising the steps of:
applying a pressing force with said external adjustment device on said outside surface of said flexible housing wall to bend said flexible side wall inwardly to move said rotor support structure axially and displacing said rotor operatively connected to said rotor support structure out of contact with and a distance away from said flat frictional surface of said inside surface of said flexible housing wall;
applying a magnetic force with said magnets of said external adjustment device to said magnets in said rotor and rotating said rotor to a desired position corresponding to a desired pressure on said valve body;
terminating applying the magnetic force to said magnets upon said rotor being rotated to the desired position; and
terminating applying said pressing force on said outside surface to permit said flexible housing wall to bend outwardly to move said rotor support structure axially to thus displace said rotor operatively connected to said rotor support structure into contact with and biased against said flexible housing wall to thus increase the frictional contact between said flat frictional surface of said rotor and said flat frictional surface of said inside surface of said flexible housing wall, and thus securing said rotor in the desired position to maintain the desired pressure on said valve body.

11. An adjustable hydrocephalus pressure control arrangement to control the pressure of the fluid in the cranium of a hydrocephalus patient, said pressure control arrangement comprising:
a housing comprising an inlet opening for permitting entry of fluid into said housing and an outlet opening for permitting exit of fluid from said housing;
said housing comprising a flexible housing wall;
said flexible housing wall comprising an inside surface and an outside surface;
said inside surface of said flexible housing wall comprising a substantially flat frictional surface;
a valve arrangement being disposed in said housing and being configured and disposed to control flow of fluid through said housing, said valve arrangement comprising:
a valve body being disposed adjacent said inlet opening;
a pressure structure being configured and disposed to apply pressure to said valve body to control flow of fluid through said inlet opening and into said housing;
a rotor being connected to said pressure structure to adjust said pressure structure to increase or decrease pressure on said valve body;
said rotor comprising magnets being configured and disposed to be acted on by an outside magnetic force to rotate said rotor in a clockwise or counterclockwise manner to adjust said pressure structure; and
said rotor comprising a substantially flat frictional surface being configured and disposed to make frictional contact with said substantially flat frictional surface of said inside surface of said flexible housing wall to thus minimize unintentional movement of said rotor; and
said flexible housing wall being configured, upon application of a pressing force on said outside surface of said flexible housing wall, to be bent to displace said rotor to thus diminish the frictional contact between said substantially flat frictional surface of said rotor and said substantially flat frictional surface of said inside surface of said flexible housing wall to permit rotation of said rotor; and
said rotor being configured and disposed, upon absence of a pressing force on said outside surface of said flexible housing wall, to be biased against said flexible housing wall to thus increase the frictional contact between said substantially flat frictional surface of said rotor and said substantially flat frictional surface of said inside surface of said flexible housing wall to minimize unintentional movement of said rotor.

12. The pressure control arrangement according to claim 11, wherein:
said flexible housing wall comprises an elastic, resilient side wall configured to resume its initial shape upon termination of a pressing force thereon;
said rotor is flat and plate-shaped and comprises a projecting lip disposed about a substantial portion of the periphery thereof; and
said substantially flat frictional surface of said rotor is disposed on said projecting lip.

13. The pressure control arrangement according to claim 12, wherein:
said flexible side wall has a thickness of one of: up to 0.5 mm and up to 0.2 mm;
said flexible side wall is configured to be deformed for the frictional contact up to a dimension that is one of: equal to twice the thickness of said flexible side wall, and up to 0.1 mm;
at least one of said housing and said flexible side wall comprises one of: a metal, titanium, and a titanium alloy; and
said pressure structure comprises a pivotable spring bar, whereby the pivoting plane of said spring bar runs parallel to the plane of motion of said rotor.

14. The pressure control arrangement according to claim 13, wherein:
said valve arrangement having a valve characteristic of variable pressure and flow generated by a metal wire or plate, the cross section of which is one of: round and rectangular, and the thickness of which is up to one of: 0.5 mm, 0.3 mm, and 0.2 mm;
the spring bar comprises a two-armed lever arm, the one lever arm of which is mechanically connected with the adjustment plate and the other lever arm of which is mechanically connected with the ball structure;
the spring bar is flexibly mounted and the mechanical connection is formed by at least one of: one lever arm being configured to slide against a cam plate of said rotor, and the other lever arm being configured to slide against said ball structure;

said two lever arms enclose an angle between them that is one of: less than 180 degrees and less than 90 degrees;

said lever arms are one of: straight and curved;

said cam plate of said rotor has one of (a) and (b): (a) a spiral shape so that when said rotor is rotated, the spring tension is varied one of: progressively and uniformly, and (b) a non-uniform profile so that the spring tension is varied unevenly; and one of (c) and (d):

(c) a trajectory of said cam disc extends over less than 360 degrees and the ends of the trajectory are limited by stops, so that the adjustment thereof results in a back-and-forth pivoting movement of said rotor; and (d) a trajectory of said cam disc extends over a peripheral angle of at least 300 degrees, and between the two ends of the spiral-shaped part a transition is provided, so that the spring, after it reaches one extreme position, moves into the other extreme position as a result of a progressive rotation of the part in the same direction with an adjustment travel of the trajectory from one of: 0.1 to 2 mm and 0.5 to 0.9 mm, whereby the actual gradient of the trajectory is determined on one hand by the actual surface area on the valve seat and on the other hand by the requirements regarding the adjustment ranges, such as toward an increasingly greater delta-p at high setting pressures.

15. The pressure control arrangement according to claim 14, wherein:

said two-armed lever spring realized comprises a pivoting bearing held with a pin that is engaged in each end in a recess in the housing;

the pin is provided with tips on its ends and pivots on the tips in the recesses;

the pin is welded or soldered to the spring;

the pin has a diameter of up to one of: 3 mm, 2 mm, and 1 mm; and said spring bar is configured to contact a portion of the surface of said ball structure.

16. The pressure control arrangement according to claim 15, wherein:

the spring makes a transition on the valve ball into a sheet;

the sheet is welded or soldered on;

each lever of said two-armed lever springs have a different cross section and comprise a rotor-side arm comprising a spring wire and a ball-side arm comprising a leaf spring;

the welded connections are laser-welded connections;

the valve arrangement has a ring-shaped housing which is provided with a base and a top, whereby a) at least the base or the cover is detachable and b) a bearing pin for the part is provided on the base or on the cover, c) in the housing ring a feed opening and a discharge opening is provided, whereby at least in one of the openings a valve ball sits which is held in the function position by the spring;

the housing has at least one of (i) and (ii): (i) an outside diameter up to one of: 31 mm and 20 mm, and (ii) a height up to one of: 10 mm and 6 mm;

the flexible side wall carries a pivot on which the rotor is rotationally mounted;

the rotor is braced against the flexible side wall for the deformation of the flexible side wall on its pivot;

the braced housing wall, for further deformation, has some freedom of movement for penetration into the rotor; and the rotor, after the stop is released, has freedom of movement with respect to the surrounding housing for the adjustment movement.

17. A method of controlling the pressure of the fluid in the cranium of a hydrocephalus patient using an adjustable hydrocephalus pressure control arrangement according to claim 11, said method comprising the steps of:

applying a pressing force on said outside surface of said flexible housing wall to bend said flexible side wall and displacing said rotor to thus diminish the frictional contact between said substantially flat frictional surface of said rotor and said substantially flat frictional surface of said inside surface of said flexible housing wall;

applying a magnetic force to said magnets in said rotor and rotating said rotor to a desired position corresponding to a desired pressure on said valve body;

terminating applying the magnetic force to said magnets upon said rotor being rotated to the desired position; and terminating applying said pressing force on said outside surface of said flexible housing wall to permit said rotor to be biased against said flexible housing wall to thus increase the frictional contact between said substantially flat frictional surface of said rotor and said substantially flat frictional surface of said inside surface of said flexible housing wall, and thus securing said rotor in the desired position to maintain the desired pressure on said valve body.

18. The pressure control arrangement according to claim 11, in combination with an external adjustment device for applying a pressing force to said flexible side wall and applying a magnetic force to said magnets of said rotor, wherein:

said external adjustment device comprises magnets, wherein said magnets of said external adjustment device and said magnets of said rotor face each other with opposite poles, so that a torque from said external adjustment device is transmitted to rotor; and said magnets have a diameter of one of: up to 3 mm and up to 1 mm, and a height of one of: up to 5 mm and up to 2 mm;

said magnets of said external adjustment device are at a distance from each other that differs from the distance between said magnets of said rotor by one of: a maximum of 3 mm and a maximum of 1 mm;

said magnets are at a maximum distance from each other of one of: 20 mm, 10 mm, and 8 mm; and said magnets of said external adjustment device in the vertical position of said external adjustment device can be moved up and down therein.

19. The combination according to claim 18, wherein:

said adjustment device is provided with a cap that can be placed on the patient's skin over the implanted pressure control arrangement;

the force provided for the elastic deformation of the housing is applied with the external adjustment device by means of an interposed spring element in the form of a power limiter;

said external adjustment device is provided with a measuring device for the adjustment movement;

said measuring device comprises at least one of: a pressure measuring device and a rotation measuring device;

said external adjustment device adjusts freely to the magnet position in the valve arrangement and the rotational position of the magnets can be read externally;

said external adjustment device comprises a reading window for reading the pressure.

20. A method of controlling the pressure of the fluid in the cranium of a hydrocephalus patient using an adjustable hydrocephalus pressure control arrangement in combination with an external adjustment device according to claim 19, said method comprising the steps of:
  applying a pressing force with said external adjustment device on said outside surface of said flexible housing wall to bend said flexible side wall and displacing said rotor to thus diminish the frictional contact between said substantially flat frictional surface of said rotor and said substantially flat frictional surface of said inside surface of said flexible housing wall;
  applying a magnetic force with said magnets of said external adjustment device to said magnets in said rotor and rotating said rotor to a desired position corresponding to a desired pressure on said valve body;
  terminating applying the magnetic force to said magnets upon said rotor being rotated to the desired position; and
  terminating applying said pressing force on said outside surface of said flexible housing wall to permit said rotor to be biased against said flexible housing wall to thus increase the frictional contact between said substantially flat frictional surface of said rotor and said substantially flat frictional surface of said inside surface of said flexible housing wall, and thus securing said rotor in the desired position to maintain the desired pressure on said valve body.

\* \* \* \* \*

UNITED STATES PATENT AND TRADEMARK OFFICE
CERTIFICATE OF CORRECTION

Page 1 of 1

PATENT NO. : 7,422,566 B2
APPLICATION NO. : 11/149928
DATED : September 9, 2008
INVENTOR(S) : Christoph Miethke It is certified that error appears in the above-identified patent and that said Letters Patent is hereby corrected as shown below:

On the cover page, after Item (65) Prior Publication Data US 2007/0004999 A1 Jan. 4, 2007, insert -- (30) Foreign Application Priority Data Dec. 11, 2002 (DE) 102 58 070.7 Oct. 8, 2003 (DE) 103 47 278.9 --.

In Column 17, Line 7 of Claim 4, after "0.2 mm", insert -- ; --.

Signed and Sealed this
Twelfth Day of July, 2011

David J. Kappos
*Director of the United States Patent and Trademark Office*